United States Patent [19]

Tanaka et al.

[11] Patent Number: 6,077,829

[45] Date of Patent: Jun. 20, 2000

[54] STABLE PHARMACEUTICAL COMPOSITION OF BDNF

[75] Inventors: Katsumi Tanaka, Takatsuki; Masashi Kumano, Mino, both of Japan

[73] Assignees: Regeneron Pharmaceuticals, Inc., Tarrytown, N.Y.; Sumitomo Pharmaceuticals Company, Limited, Osaka-fu, Japan

[21] Appl. No.: 09/180,884

[22] PCT Filed: May 26, 1997

[86] PCT No.: PCT/JP97/01746

§ 371 Date: Nov. 16, 1998

§ 102(e) Date: Nov. 16, 1998

[87] PCT Pub. No.: WO97/45135

PCT Pub. Date: Dec. 4, 1997

[30] Foreign Application Priority Data

May 27, 1996  [JP]  Japan ..................................... 8-156070

[51] Int. Cl.⁷ ..................................................... A61K 38/22
[52] U.S. Cl. ................................................ 514/21; 514/12
[58] Field of Search ........................ 514/12, 21; 530/350, 530/399

[56] References Cited

U.S. PATENT DOCUMENTS

| 5,180,820 | 1/1993 | Barde et al. | 536/23.51 |
| 5,604,202 | 2/1997 | Kessler et al. | 514/12 |
| 5,770,577 | 6/1998 | Kinstler et al. | 514/21 |

FOREIGN PATENT DOCUMENTS 9107947  6/1991  WIPO.

OTHER PUBLICATIONS

T, Arakawa, Tanpakushitsu, Kakusan, Koso (Protein, Nucleic Acid, Enzyme) 37(9), 1517 (1992).

*Primary Examiner*—Jeffrey E. Russel
*Attorney, Agent, or Firm*—Birch, Stewart, Kolasch & Birch, LLP

[57] ABSTRACT

A stable pharmaceutical composition of brain derived neurotrophic factor (BDNF) in the form of an aqueous solution or lyophilized one being suitable for a long-term storage, which contains a surfactant, especially nonionic surfactant (e.g., Tween 80) of 0.001 to 10%, whereby the polymerization and the denaturation of BDNF are inhibited, and the biological activities of BDNF are maintained for a long time. The lyophilized composition can be made more stable by addition of a sugar alcohol (e.g., mannitol) and/or an amino acid (e.g., glycine).

17 Claims, No Drawings

STABLE PHARMACEUTICAL COMPOSITION OF BDNF

This application is the national phase under 35 U.S.C. §371 of prior PCT International Application No. PCT/J97/01746 which has an International filing date of May 26, 1997 which designated the United States of America, the entire contents of which are hereby incorporated by reference.

TECHNICAL FIELD

The present invention relates to a pharmaceutical composition containing a brain derived neurotrophic factor (BDNF) in the form of an aqueous solution or a lyophilized one, the latter being prepared by lyophilizing said aqueous solution composition.

BACKGROUND ART

Nerve cells of vertebrata need a certain group of polypeptides, called a neurotrophic factor, for their survival. As one of the neurotrophic factors, a brain derived neurotrophic factor (BDNF) has been known. BDNF has first been isolated from porcine brain by Barde, Y. E. et al. (cf., The EMBO Journal, 5, 549–553 (1982)), and thereafter BDNF genes of pig, human and mouse have been cloned in 1989 whereby it has been confirmed that it has a primary structure consisting of 119 amino acids (cf., Leibrock, J. et al., Nature, 341, 149 (1989)). Recently, a lot of attention has been given to BDNF because BDNF is considered to play a very important role in the central nervous system.

BDNF is a polypeptide exhibiting various pharmacological activities in the nervous system, and the pharmacological activities thereof have been disclosed in Seitai no Kagaku (Science of Living body), 43 (6), 616–625 (1992). Besides, BDNF has been expected to be useful as an agent for treatment of various diseases such as amyotrophic lateral sclerosis (ALS), anticancer agent-intoxicated neuropathy, diabetic neuropathy, retinal pigment degeneration, glaucoma, Huntington's chorea, Parkinson disease, Alzheimer's disease, terminal cancer ache, depression, obesity, etc., based on the pharmacological activities thereof (cf., U.S. Pat. No. 5,180,820, Seitai no Kagaku, 43 (6), pages 616–625, (1992)).

A compound to be used as a medicament is usually required to be stable without a change in the activity thereof over time under conventional storage conditions when formulated in a form of a conventional pharmaceutical composition. Especially, highly purified polypeptides such as BDNF have many problems to be solved in order to be kept stably for a long time. For example, when keeping BDNF in the form of a solution in a conventional physiological saline solution, BDNF has a tendency to aggregate even where stored for several days to dozens of days, which is a very serious problem. The aggregate of BDNF is known to cause immune toxicity to the living body, so that the prevention of the production of BDNF aggregate is very important. Besides, denatured and/or polymerized BDNF are often produced as well. Hitherto, there has been no report on effective ways to solve these serious problems of BDNF.

In general, when a compound of a low molecular weight is unstable in the form of an aqueous solution, the solution is usually tried to be lyophilized for stabilization. However, polypeplides are known not to be stable during the lyophilization procedures (cf., Tanpakushitsu, Kakusan, Koso (i.e., Protein, Nucleic Acid, Enzyme), 37 (9), 1517 (1992)). Besides, the conventional stabilizers exhibit their stabilization effects in an aqueous solution of a polypeptide by supporting hydration between a water molecule and a polypeptide. Therefore, these stabilizers cannot exhibit their stabilization effects in a lyophilized composition in many cases because no water molecule exists therein (cf., Tanpakushitsu, Kakusan, Koso (i.e., Protein, Nucleic Acid, Enzyme), 37 (9), 1517 (1992)). Hitherto, a lyophilized pharmaceutical composition of BDNF has been known, and any skilled person in the art cannot imagine the physicochemical and biological stability of the lyophilized pharmaceutical composition of BDNF.

DISCLOSURE OF INVENTION

When keeping BDNF at a low temperature or room temperature for several days to dozens of days, BDNF aggregates, shows varied properties, and denatured and/or polymerized BDNF are produced. Thus, the physicochemical stability of BDNF is low so that BDNF cannot be kept for a long time. The instability has prohibited the development of BDNF as a medicament for human or for other animals in the form of a pharmaceutical preparation such as an injection preparation.

Under the above-mentioned circumstances, the present inventors have intensively studied to develop a pharmaceutical composition of BDNF, and have found that the addition of a surfactant is quite effective for the stabilization of BDNF, and have accomplished the present invention.

That is, the present invention provides a stable pharmaceutical composition of a brain derived neurotrophic factor (BDNF), which comprises as an active ingredient a BDNF and as a stabilizer a surfactant, preferably a nonionic surfactant, and optionally a salt and/or a buffering agent, and further optionally an additional stabilizer such as an amino acid and a sugar alcohol, which may be in the form of an aqueous solution, or in a lyophilized form.

The present invention provides also a method for stabilizing a BDNF in a pharmaceutical composition by incorporating a surfactant as a stabilizer into the composition and optionally further adding a salt and/or a buffering agent and further optionally adding an additional stabilizer such as an amino acid and a sugar alcohol.

Embodiments of the composition of the present invention are exemplified below.

(1) A stable pharmaceutical composition, which comprises a BDNF and a surfactant.

(2) The pharmaceutical composition according to (1), wherein the surfactant is a nonionic surfactant.

(3) The pharmaceutical composition according to (2), wherein the nonionic surfactant is Tween 80.

(4) The pharmaceutical composition according to (3), wherein the Tween 80 is contained in an amount of 0.001% (w/v) to 10% (w/v).

(5) The pharmaceutical composition according to (1), which further comprises a salt.

(6) The pharmaceutical composition according to (5), wherein the salt is sodium chloride.

(7) The pharmaceutical composition according to (1), which further comprises a buffering agent.

(8) The pharmaceutical composition according to (7), wherein the buffering agent is a phosphate buffer.

(9) The pharmaceutical composition according to (1), which has a pH value in the range of 5.5 to 7.5.

(10) The pharmaceutical composition according to (1), which is in the form of a lyophilized composition.

(11) The pharmaceutical composition according to (10), which further comprises an additional stabilizer.

(12) The pharmaceutical composition according to (11), wherein the additional stabilizer is a member selected from an amino acid and a sugar alcohol, or a combination thereof.

(13) The pharmaceutical composition according to (12), wherein the amino acid is glycine, and the sugar alcohol is mannitol.

(14) The pharmaceutical composition according to (11), wherein the additional stabilizer is contained in the range of 0.1 to 10% by weight to the weight of BDNF.

(15) A lyophilized pharmaceutical composition of BDNF which contains as a stabilizer Tween 80 and as an additional stabilizer mannitol in the total amount of from 0.01% (w/v) to 10% (w/v), based on the whole weight of the reconstituted composition.

The BDNF used in the present invention may be any one of any animal origin, such as mouse, pig, or human, and can be prepared by various processes. When a BDNF isolated from animal tissues is used in the present invention, it may be purified to such a degree that it can be used as a medicament (cf., The EMBO Journal, 5, 549–553 (1982)). Alternatively, a BDNF can be obtained by culturing a primary culture cell or an established cell line which can produce BDNF, and isolating from the culture broth thereof (e.g., culture supernatant, cultured cells). Moreover, there may be used a recombinant BDNF which can be obtained by a conventional gene engineering technique, e.g., by inserting a gene coding for BDNF into a suitable vector, transforming a suitable host with the recombinant vector, and isolating from the culture supernatant of the resulting transformant (cf., Proc. Natl. Acad. Sci. U.S.A., 88, 961 (1991); Biochem. Biophys. Res. Commun., 186, 1553 (1992)), which is suitable for production of BDNF of uniform property in a large scale. The host cells to be used in the above process are not critical, and may be any conventional host cells which have been used in gene engineering techniques, for example, *Escherichia coli, Bacillus subtilis*, yeasts, vegetable cells or animal cells.

A modified protein of BDNF can be obtained by addition, substitution, deletion or removal of a part of amino acid sequence of a natural BDNF by a gene engineering technique. Any modified protein of BDNTF thus obtained is also included in the BDNF to be used in the present invention even though a part of the amino acid sequence thereof is deleted, or substituted by other amino acid, or inserted thereto a part of other amino acid sequence, or bonded with one or more amino acids at the N-terminus and/or C-terminus, as long as said modified protein of BDNF shows the biological activities of the same quality as those of BDNF, i.e., the biological activities on the nerve cells, such as an activity of survival of nerve cells, activity of extending neurodendrite, activity of promoting the production of neurotransmitter. That is, in addition to mature BDNFs, Met-BDNF having a methionine at the N-terminus of BDNF, etc. can be used in the present composition as long as it shows the neurotrophic activities of the same quality as those of natural BDNFs.

The "surfactant" used in the present invention means any pharmaceutically acceptable surfactant which is useful in medicaments for human, or for other animals, and includes, for example, a nonionic surfactant. The most preferable surfactant is Tween 80 (Polysorbate 80=polyoxyethylene sorbitan mono-oleate), or Tween 20 (Polysorbate 20=polyoxyethylene sorbitan mono-laurate), Pluronic F-68 (=a polyoxyethylene polyoxypropylene glycol), polyethylene glycol, etc. The surfactant is added to the pharmaceutical composition of the present invention in an amount of from 0.001 to 10% by weight, preferably in an amount of from 0.001 to 0.1% by weight, to the weight of water in the aqueous composition.

The "salt" may be a pharmaceutically acceptable salt which is useful in medicaments for human, or for other animals, and includes, for example, sodium chloride. Sodium chloride is used in order to keep the osmotic pressure of the present pharmaceutical composition suitable for an injection preparation, especially in an amount of 150 to 300 mM by which the injection preparation shows an osmotic pressure ratio of 1 to 2.

The "buffering agent" means a buffering agent which is added to the composition in order to adjust the pH value in a solution preparation or in a lyophilized preparation, in the latter preparation, the pH when reconstituted. The representative buffering agent is, for example, phosphate buffer, Tris buffer and citrate buffer. The buffering agent adjusts the pH value of the solution so that the stability of BDNF is maintained. The pH value of the present composition is not critical, but it is preferably in the range of 5.5 to 7.5. BDNF is hydrolyzed under acidic conditions to produce many fragments derived from BDNF, and is further de-amidated or hydrolyzed under basic conditions. The final concentration of the buffering agent in the composition is in the range of 1 mM to 100 mM.

The "additional stabilizer" includes, for example, amino acids such as glycine or sugar alcohols such as mannitol, and these additional stabilizers may be used together. When preparing the pharmaceutical composition of BDNF with the additional stabilizer, the storage stability of BDNF in the preparation is further improved. The additional stabilizer, for example, glycine or mannitol, is added in an amount of from 0.01 to 100 times by weight, more preferably 0.1 to 10 times by weight, of the weight of BDNF. Glycine and/or mannitol can be used in a solution composition of the present invention, but can show more excellent stabilization effects in the lyophilized composition of the present invention. These amino acid and sugar alcohol may be used individually, but preferably in combination.

The "lyophilized composition" of the present invention can be prepared by subjecting a solution composition of BDNF to lyophilization by a conventional lyophilization, or freeze-drying technique. For example, BDNF is dissolved in a suitable aqueous solvent such as a distilled water for injection, a buffer solution, a physiological saline solution, etc., and thereto is added a stabilizer, a buffering agent, or a salt, if necessary, and the solution thus obtained is sterilized by filtration through a filter, and then lyophilized to give a lyophilized composition of the present invention.

The compositions of the present invention may additionally contain a conventional additive which is usually used for pharmaceutical preparations, for example, a solubilizer, antioxidant, anaesthetic agent, isotonic agent, etc. The lyophilizing method is, for example, a method consisting of three steps: a step of freezing a solution under atmospheric pressure, a primary drying step of sublimation of a free water which is not adsorbed by or bound to a solute under reduced pressure, and a secondary drying step of removing water adsorbed by or bound to a solute (cf., Pharm. Tech. Japan, 8 (1), 75–87 (1992)). BDNF to be contained in the composition can be kept very stably during the procedures of preparing the composition of the present invention, such as dissolving in a solvent, freeze-drying thereof, as well as reconstituting a lyophilized composition.

The content of BDNF in the compositions may be varied depending on the kinds of diseases to be cured, or the administration route thereof.

The pharmaceutical composition of BDNF of the present invention may be filled in a vial by putting BDNF in a vial, filling the vial with nitrogen gas, and then sealing the vial. When the vial is filled with nitrogen gas, BDNF contained therein is prevented from denaturing and hence can be kept more stably.

BEST MODE FOR CARRYING OUT THE INVENTION

The present invention is illustrated in more detail by the following Examples, but should not be construed to be limited thereto.

EXAMPLE 1

Effects of Surfactant 1
Preparation of a Solution Composition of BDNF Without a Surfactant (Reference Solution Composition 1)

BDNF was dissolved in 10 mM phosphate buffer (pH 7.0, 150 mM sodium chloride) to give an aqueous BDNF solution (20 mg/ml). The solution thus obtained was put into vials aseptically to give a solution composition of BDNF containing no surfactant.
Preparation of a Solution Composition of BDNF With a Surfactant (Present Solution Composition 1)

BDNF was dissolved in 10 mM phosphate buffer (pH 7.0, 150 mM sodium chloride, 0.01% Tween 80) to give an aqueous BDNF solution (20 mg/ml). The solution thus obtained was put into vials aseptically to give a solution composition of BDNF containing a surfactant.
Experiment 1

Using Reference Solution Composition 1 and Present Solution Composition 1, the inhibitory effect of a surfactant on the production of aggregates was tested. The compositions were kept at 25° C. at a vibration of 5 cm×75 strokes/min. The period (days) till the production of aggregates was determined by visual observation. The results are shown in Table 1. From the resulting data, it is proved that the addition of Tween 80 inhibited the production of aggregates of BDNF in a solution composition.

TABLE 1

Effects of Tween 80 on the production of aggregartes of BDNF (n = 5)

|  | Concentration of Tween 80 (%) | Period for the production of aggregate (days) |
|---|---|---|
| Reference Solution Composition 1 | 0 | 10 |
| Present Solution Composition 1 | 0.01 | >30 |

EXAMPLE 2

Effects of Surfactant 2
Preparation of a Solution Composition of BDNF Without a Surfactant (Reference Solution Composition 2)

BDNF was dissolved in 10 mM phosphate buffer (pH 7.0, 150 mM sodium chloride) to give an aqueous BDNF solution (0.1 mg/ml). The solution thus obtained was put into vials aseptically to give a solution composition of BDNF containing no surfactant.
Preparation of a Solution Composition of BDNF With a Surfactant (Present Solution Composition 2)

BDNF was dissolved in 10 mM phosphate buffer (pH 7.0, 150 mM sodium chloride, 0.01% Tween 80) to give an aqueous BDNF solution (0.1 mg/ml). The solution thus obtained was put into vials aseptically to give a solution composition of BDNF containing a surfactant.
Experiment 2

Using Reference Solution Composition 2 and Present Solution Composition 2, the inhibitory effect of a surfactant on the adsorption of BDNF onto the vessel was tested. The concentration of BDNF was determined by absorption spectrophotometry immediately after and before the BDNF solution was put into a glass vial, and the amount of BDNF adsorbed onto the glass vial was calculated. The results are shown in Table 2. From the results, it is proved that the addition of Tween 80 reduced the adsorption amount of BDNF onto the glass vial in a solution composition.

TABLE 2

Effects of Tween 80 on the adsorption of BDNF onto the glass surface

|  | Concentration of Tween 80 (%) | Adsorbed BDNF on the surface of glass vial ($\mu g/cm^2$) |
|---|---|---|
| Reference Solution Composition 1 | 0 | 0.73 |
| Present Solution Composition 2 | 0.01 | 0.28 |

EXAMPLE 3

Effects of pH
Preparation of a Solution Composition of BDNF (Present Solution Composition 3)

BDNF was dissolved in 10 mM phosphate buffer (pH 7.0, 150 mM sodium chloride, 0.01% Tween 80) to give an aqueous BDNF solution (5 mg/ml). The pH value of the aqueous BDNF solution thus obtained was adjusted with 1N HCl or 1N NaOH to six degrees of pH 4, 5, 6, 7, 8 or 9. The solutions thus obtained was put into vials aseptically to give a solution composition of BDNF.
Preparation of a Lyophilized Composition of BDNF (Present Lyophilized Composition 3)

BDNF was dissolved in 10 mM phosphate buffer (pH 7.0, 150 mM sodium chloride, 0.01% Tween 80) to give an aqueous BDNF solution (20 mg/ml). The solution thus obtained was put into vials aseptically, and lyophilized under the conditions as shown in Table 3 to give a lyophilized BDNF composition. In Table 3, the mark → means that the temperature was changed.

TABLE 3

Lyophilization conditions

|  | Freezing step | | Primary drying step | | Secondary drying step | |
|---|---|---|---|---|---|---|
| Temperature (° C.) | 5 → −40 | −40 | −40 → 0 | 0 | 0 → 20 | 20 |
| Period (hr) | 1 | 10 | 8 | 24 | 1 | 24 |
| Pressure (mmHg) | 760 | 760 | <1 | <1 | <1 | <1 |

Experiment 3

Using Present Solution Composition 3 and Present Lyophilized Composition 3, the effects of pH value on the storage stability of BDNF was studied. The compositions obtained above were kept at 25° C. or 40° C. for three months, and the contents of BDNF, polymerized BDNF and denatured BDNF were determined by the methods mentioned hereinbelow. As shown in Table 4, the content of BDNF was reduced under basic conditions, but slightly reduced under acidic conditions. The polymerized BDNF was hardly produced under acidic conditions, but increased under basic conditions. On the other hand, the content of the denatured BDNF was more increased under acidic conditions than under basic conditions.

Method for Determnining the BDNF Content

BDNF was diluted to 2 mg/ml, and the concentration thereof was determined by reverse phase chromatography under the following conditions.

Column: VYDAC214BTPC4

Solvent: Solution A: 0.1% aqueous trifluoroacetic acid solution

Solution B: 0.1% trifluoroacetic acid solution in acetonitrile

Graduation Conditions

The concentration (%) of Solution B was 26, 35, 35, 90, 26 and 26 at a time (minutes) of 0, 36, 42, 46, 47, 66, respectively.

Detection: 215 nm

Flow rate: 1.0 ml/min.

Temperature: 60° C.

Apply: 25 μl

Method for Determining the Polymerized:Denatured BDNF

Method for Determining the BDNF Content

BDNF was diluted to 2 mg/ml, and the concentration thereof was determined by gel filtration chromatography under the following conditions.

Column: SUPERDEX75HR

Solvent: 300 mM sodium phosphate, 500 mM sodium chloride, 5% n-propanol, pH 6

Detection: 215 nm

Flow rate: 0.6 ml/min

Apply: 10 μl

TABLE 4

Effects of pH value on the BDNF stability

| pH | Temperature (° C.) | Storage period (month) | Content* of BDNF (%) | Content* of polymerized BDNF (%) | Content* of denatured BDNF (%) |
|---|---|---|---|---|---|
| 7 | — | Initial | 93.58 | 0.00 | 0.0 |
| 4 | 25 | 3 | 93.54 | 0.00 | 1.19 |
|   | 40 | 3 | 90.06 | 0.03 | 2.07 |
| 5 | 25 | 3 | 92.98 | 0.04 | 0.18 |
|   | 40 | 3 | 87.87 | 0.05 | 1.85 |
| 6 | 25 | 3 | 92.77 | 0.05 | 0.24 |
|   | 40 | 3 | 90.45 | 0.12 | 0.84 |
| 7 | 25 | 3 | 9.059 | 0.23 | 0.11 |
|   | 40 | 3 | 79.78 | 0.72 | 0.49 |
| 8 | 25 | 3 | 86.69 | 0.66 | 0.00 |
|   | 40 | 3 | 60.61 | 3.01 | 0.36 |
| 9 | 25 | 3 | 83.96 | 1.07 | 0.12 |
|   | 40 | 3 | — | 3.45 | 0.41 |

*: The ratio to the total peak area.

EXAMPLE 4

Stability During the Lyophilization Procedures, and Effects of the Composition Forms Preparation of a Solution Composition of BDNF (Present Solution Composition 4)

BDNF was dissolved in 10 mM phosphate buffer (pH 7.0, 150 mM sodium chloride, 0.01% Tween 80) to give an aqueous BDNF solution (5 mg/ml). The solution thus obtained was put into vials aseptically, and the vials were fulfilled with nitrogen gas, and then sealed to give a solution composition of BDNF.

Preparation of a Lyophilized Composition of BDNF (Present Lyophilized Composition 4)

BDNF was dissolved in 10 mM phosphate buffer (pH 7.0, 150 mM sodium chloride, 0.01% Tween 80) to give an aqueous BDNF solution (5 mg/ml). The solution thus obtained was put into vials aseptically, and lyophilized under the conditions as shown in Table 3 to give a lyophilized composition of BDNF. The vials were fulfilled with nitrogen gas and were sealed.

Experiment 4

In order to study the stability of BDNF during the lyophilization procedures, the content of BDNF and the biological activities thereof were determined in a solution composition of BDNF before the lyophilization procedures in Example 4, and in re-dissolved aqueous solution of the lyophilized composition by the method as mentioned hereinbelow. The results are shown in Table 5. The significant changes were not recognized before and after the lyophilization procedures, by which it is proved that BDNF is stable during the lyophilization procedures and the re-dissolving step thereafter, and that BDNF can be formulated into a form of a lyophilized composition.

Method for Determining the Biological Activities of BDNF

The biological activities of BDNF were determined based on the cell proliferation potency of BAF-trkB cells when treated with BDNF. Said BAF-trkB cells were prepared by introducing a trkB gene (a BDNF receptor) into IL3-dependent pre-B cells (cf., Cell, 41, 727–734, July 1985) in the same manner as described in U.S. Pat. No. 5,622,862.

TABLE 5

Stability of BDNF during the lyophilization procedures

| | Biological activities (specific activity: × $10^4$ TU/mg) | Content of BDNF (%) |
|---|---|---|
| Present Solution Composition 4 | 1.33 ± 0.21 | 93.34 |
| Immediately after re-dissolution of Present Lyophilized Composition 4 | 1.61 ± 0.30 | 93.14 |

Experiment 5

In order to study the differences in the storage stability between the solution composition and the lyophilized composition of BDNF, the BDNF contents in the compositions prepared in Example 4 were determined immediately after the preparation thereof, or after three-month storage at 25° C., or 40° C. The results are shown in Table 6. In the lyophilized composition, the content of polymerized BDNF was slightly higher than that in the solution composition, but the content of BDNF per se is higher, and the content of the denatured BDNF was lower, than that in the solution composition.

TABLE 6

Effects of the composition forms on the stability of BDNF

| Formulation | Temperature (° C.) | Storage period (month) | BDNF content (%) | Content of polymerized BDNF (%) | Content of denatured BDNF (%) |
| --- | --- | --- | --- | --- | --- |
| Present | — | Initial | 92.91 | 0.09 | 0 |
| Solution | 25 | 3 | 91.21 | 0.26 | 0.24 |
| Composition 4 | 40 | 3 | 86.21 | 0.38 | 0.75 |
| Present | — | Initial | 93.71 | 0.07 | 0.0 |
| Lyophilized | 25 | 3 | 92.82 | 0.34 | 0.0 |
| composition 4 | 40 | 3 | 88.40 | 1.66 | 0.0 |

EXAMPLE 5

Effects of Surfactant 5

Preparation of a Lyophilized Composition of BDNF With a Surfactant (Present Lyophilized Composition 5)

A lyophilized composition of BDNF was prepared by the same method as in Example 4 to give Present Lyophilized Composition 5.

Preparation of a Lyophilized Composition of BDNF Without a Surfactant (Reference Lyophilized Composition 5)

BDNF was dissolved in 10 mM phosphate buffer (pH 7.0, 150 mM sodium chloride) to give an aqueous BDNF solution (5 mg/ml). The solution thus obtained was put into vials aseptically, and lyophilized under the same conditions as shown in Table 3 to give a lyophilized composition of BDNF. The vials were fulfilled with nitrogen gas and sealed.

Experiment 6

In order to study the effects of a surfactant on the appearance of the re-dissolved solution of a lyophilized composition, Reference Lyophilized Composition 5 and Present Lyophilized Composition 5 were dissolved in purified water, and the appearance of these solutions was visually observed. The results are shown in Table 7. When reconstituting Present Lyophilized Composition 5, the solution was clear, while the solution of Reference Lyophilized Composition 5 wherein no surfactant was added was turbid after the dissolution thereof.

TABLE 7

Effects of surfactant on the appearance of re-dissolved solution of the lyophilized composition

| | Tween 80 | Appearance of the re-dissolved solution |
| --- | --- | --- |
| Present Lyophilized Composition 5 | 0.01% | Clear |
| Reference Lyophilized Composition 5 | Not added | Turbid |

EXAMPLE 6

Effects of Stabilizer on the Stability of the Lyophilized Composition of BDNF

Preparation of a Lyophilized Composition of BDNF with a Surfactant (Present lyophilized composition 6A)

A lyophilized composition of BDNF was prepared by the same method as in Example 4 to give Present Lyophilized Composition 6A.

Preparation of a Lyophilized Composition of BDNF Without a Surfactant (Present Lyophilized Composition 6B)

BDNF was dissolved in 10 mM phosphate buffer (pH 7.0, 150 mM sodium chloride, 0.01% Tween 80) to give an aqueous BDNF solution (5 mg/ml). To the solution was added mannitol so that the final concentration of mannitol was 10 mg/ml. The aqueous solution of BDNF thus obtained was put into vials aseptically, and lyophilized under the same conditions as shown in Table 3 to give a lyophilized composition of BDNF. The vials were fulfilled with nitrogen gas and sealed.

Preparation of a Lyophilized Composition of BDNF With a Surfactant (Present Lyophilized Composition 6C)

BDNF was dissolved in 10 mM phosphate buffer (pH 7.0, 150 mM sodium chloride, 0.01% Tween 80) to give an aqueous BDNF solution (5 mg/ml). To the solution was added glycine so that the final concentration of glycine is 10 mg/ml. The aqueous solution thus obtained was put into vials aseptically, and lyophilized under the conditions as shown in Table 3 to give a lyophilized composition of BDNF. The vials were fulfilled with nitrogen gas and sealed.

Experiment 7

Using Present Lyophilized Compositions 6A, 6B and 6C, the content of BDNF was determined immediately after the preparation, or after one-month storage at 40° C. The results are shown in Table 8. In addition, using Present Lyophilized Compositions 6A and 6B, the content of BDNF was also determined immediately after the preparation, or after three-month storage at 25° C. or 40° C. The results are shown in Table 9. The compositions containing a stabilizer showed a higher stability than the composition containing no stabilizer.

TABLE 8

Effects of stabilizer in Lyophilized Compositions 1

| | Stabilizer | Temperature | Storage period | Content of BDNF |
| --- | --- | --- | --- | --- |
| Present Lyophilized Composition 6A | Not added | —<br>40 | Initial<br>1 | 91.98<br>78.69 |
| Present Lyophilized Composition 6B | Mannitol | —<br>40 | Initial<br>1 | 92.16<br>86.74 |
| Present Lyophilized Composition 6C | Glycine | —<br>40 | Initial<br>1 | 92.20<br>83.99 |

Note: In Composition 6A, 6B and 6C used in this experiment, the vials were not fulfilled with nitrogen gas.

TABLE 9

Effects of stabilizer in Lyophilized Compositions 2

| | Stabilizer | Temperature (° C.) | Storage period (month) | Content of BDNF (%) | Content of polymerized BDNF (%) | Content of denatured BDNF (%) |
|---|---|---|---|---|---|---|
| Present Composition 6A | Not added | — | Initial | 93.71 | 0.07 | 0.0 |
| | | 25 | 3 | 92.82 | 0.34 | 0.0 |
| | | 40 | 3 | 88.40 | 1.66 | 0.0 |
| Present Composition 6B | Mannitol | — | Initial | 93.03 | 0.16 | 0.0 |
| | | 25 | 3 | 92.85 | 0.18 | 0.02 |
| | | 40 | 3 | 92.55 | 0.37 | 0.0 |

INDUSTRIAL APPLICATION

The pharmaceutical composition of BDNF of the present invention can maintain BDNF stable for a long time by adding thereto a surfactant. The present compositions of BDNF show the following effects:

(1) prevention of the production of turbidness or aggregations of BDNF in a pharmaceutical solution composition of BDNF of the present invention, during the storage thereof;

(2) prevention of the production of turbidness or aggregations of BDNF, when dissolving a lyophilized pharmaceutical composition of BDNF of the present invention;

(3) prevention of the adsorption of BDNF onto a surface of a glass or resin vessel therefor; and (4) reservation of the biological activities of BDNF.

The pharmaceutical composition of BDNF containing a salt as an isotonic agent, a buffering agent for keeping an optimal pH value, or containing both of these salt and buffering agent may be in the form of a pharmaceutical composition being suitable for clinical use. The stability of BDNF contained in the pharmaceutical solution composition of the present invention is more improved when lyophilized.

The lyophilized pharmaceutical composition of BDNF of the present invention additionally containing as an additional stabilizer an amino acid and/or a sugar alcohol is more stable. Especially, the lyophilized composition of BDNF containing glycine as an amino acid and/or mannitol as a sugar alcohol is the most stable composition.

What is claimed is:

1. A pharmaceutical composition of a brain derived neurotrophic factor (BDNF), which comprises a BDNF and a nonionic surfactant in admixture with a pharmaceutically acceptable carrier or diluent wherein the nonionic surfactant is polyoxyethylene sorbitan mono-oleate.

2. The pharmaceutical composition according to claim 1, wherein polyoxyethylene sorbitan mono-oleate is contained in an amount from 0.001% (w/v) to 10% (w/v).

3. The pharmaceutical composition according to claim 1, which further comprises a salt.

4. The pharmaceutical composition according to claim 3, wherein the salt is sodium chloride.

5. The pharmaceutical composition according to claim 1, which further comprises a buffering agent.

6. The pharmaceutical composition according to claim 5, wherein the buffering agent is a phosphate buffer.

7. The pharmaceutical composition according to claim 1, which has a pH value in the range of 5.5 to 7.5.

8. The pharmaceutical composition according to claim 1, which is in the form of a lyophilized composition.

9. The pharmaceutical composition according to claim 8, which further comprises an additional stabilizer.

10. The pharmaceutical composition according to claim 9, wherein the additional stabilizer is a member selected from the group consisting of an amino acid and a sugar alcohol, or a combination thereof.

11. The pharmaceutical composition according to claim 10, wherein the amino acid is glycine, and the sugar alcohol is mannitol.

12. The pharmaceutical composition according to claim 9, wherein the additional stabilizer is contained in the range of 0.1 to 10% by weight to the weight of BDNF.

13. A lyophilized pharmaceutical composition of BDNF which contains as a stabilizer polyoxyethylene sorbitan mono-oleate and as an additional stabilizer mannitol in a total amount of from 0.01% (w/v) to 10% (w/v), based on the total weight of the composition when reconstituted in an aqueous medium.

14. A method for stabilizing a BDNF in a pharmaceutical composition, which comprises incorporating a nonionic surfactant into a pharmaceutical composition of a BDNF wherein the nonionic surfactant is polyoxyethylene sorbitan mono-oleate.

15. The method according to claim 14, wherein the pharmaceutical composition of a BDNF further comprises a salt and/or a buffering agent.

16. The method of according to claim 14, wherein the pharmaceutical composition comprising the nonionic surfactant is in the form of a lyophilized composition.

17. The method according to claim 16, which further comprises adding an additional stabilizer selected from the group consisting of an amino acid, a sugar alcohol, and a combination thereof.

* * * * *